United States Patent [19]

Sever, Jr.

[11] Patent Number: 6,057,846
[45] Date of Patent: May 2, 2000

[54] VIRTUAL REALITY PSYCHOPHYSIOLOGICAL CONDITIONING MEDIUM

[76] Inventor: Frank Sever, Jr., P.O. Box 7500, Arlington, Va. 22207

[21] Appl. No.: 08/961,146

[22] Filed: Oct. 30, 1997

Related U.S. Application Data

[63] Continuation-in-part of application No. 08/639,933, Apr. 26, 1996, Pat. No. 5,736,986, which is a continuation-in-part of application No. 08/502,362, Jul. 14, 1995, Pat. No. 5,742, 748.

[51] Int. Cl.⁷ ............................................ A63B 24/00
[52] U.S. Cl. ............................................... 345/419
[58] Field of Search .................................... 345/418, 419, 345/420; 128/774; 434/307, 247; 463/36

[56] References Cited

U.S. PATENT DOCUMENTS

| | | | |
|---|---|---|---|
| 4,060,915 | 12/1977 | Conway | 434/307 |
| 5,229,756 | 7/1993 | Kosugi et al. | 436/36 |
| 5,429,140 | 7/1995 | Burdea et al. | 128/774 |

*Primary Examiner*—Phu K. Nguyen
*Assistant Examiner*—Cliff N. Vo

[57] ABSTRACT

The instant invention provides a medium including a program operable within a virtual reality device which is designed for perfecting mental visualization within the mind of a subject sufficient alone to effect a desired neurological and/or physiological change within the body of the subject, even in the substantial absence of any physical movement by the subject. The program includes a dynamic scenario that is designed to communicate in chronological order: (I.) a condition which requires a remedy; (ii.) a mode for effecting the remedy; (iii.) the performance of the mode so as to effect the remedy; and, (iv.) rectification of the condition through the performance of the mode. The program is interspersed with audible, visual or combined audible/visual subliminal stimuli, designed to aid a subject in achieving the goal. It also provides the medium in combination with a virtual reality device and a method of using the same. The steps of the method include: operatively interfacing the program with the device and mounting the device on the subject; and, running the program. Optionally, the program can be designed to precondition of the subject's mind, such as inducing a state of meditation or hypnosis, or combinations thereof, and thereafter communicate a metaphoric or real, or combined real and metaphoric, scenario to the subject. The scenario of the program can be designed to exist in real time, real space, compressed time, compressed space, expanded time, expanded space, or any combination thereof, real or metaphoric or any combination of real and metaphoric. Optionally the program is further designed to enable (motor) interaction between the subject and/or an operator external to the preconditioning and the device.

16 Claims, No Drawings

VIRTUAL REALITY PSYCHOPHYSIOLOGICAL CONDITIONING MEDIUM

RELATED APPLICATIONS

This is a Continuation-in-part of application Ser. No. 08/639,933, filed Apr. 26, 1996, now U.S. Pat. No. 5,736,986, entitled: VIRTUAL REALITY MENTAL CONDITIONING MEDIUM, which is a Continuation-in-part of application Serial No. 08/502,362, filed Jul. 14, 1995, now U.S. Pat. No. 5,742,748, entitled: VIRTUAL REALITY MENTAL CONDITIONING MEDIUM.

BACKGROUND OF THE INVENTION

This invention in its broadest aspects contemplates the application of subliminal conditioning to virtual reality technology for perfecting the mental visualization skills of a subject sufficient alone to effect a desired neurological and/or physiological change within the body of said subject characteristic of: mental learning, physical learning, mental training, physical training, mental healing, physical healing, and combinations thereof, even in the substantial absence of any physical movement by said subject. The program includes at one subliminal stimulus selected from the group of audible subliminal stimulus, visual subliminal stimulus and combinations.

DESCRIPTION OF THE PRIOR ART

Virtual Reality

The emerging art of virtual reality is now becoming well known as exemplified by the following prior art references which are incorporated herein by reference in their entireties:

U.S. Pat. No. 5,394,517; issued Feb. 28, 1995; assigned to BRITISH AEROSPACE; and classified at United State Patent Office (USPTO) classification(s)/subclassification(s) 395/129 395/135; and entitled: Integrated Real and Virtual Environment Display System, relates to improvements in so-called "virtual reality" computer systems. The display system described enables the effective integration of computer generated images and real, naturally occurring images in the visual display units which provide the user with his entire visual stimulation. Areas of the user's notional field of view where computer-generated imagery is required (for example the cockpit canopy in an aircraft flight simulator) are colored with a predetermined color or intensity. Two video cameras are provided, each of which is mounted so that its field of view corresponds to a respective one of the notional fields of view of the user's eyes. The signals from the video cameras are analyzed to determine the presence of the predetermined color or intensity, thereby giving an indication that a computer generated image is required for that part of the video camera's field of view. If the predetermined color or intensity is not present, the signal from the video camera is relayed directly to the appropriate one of the visual display units.

U.S. Pat. No. 5,389,865; issued Feb. 14, 1995; assigned to CYBERNET SYSTEMS CORPORATION; classified at USPTO classification 318/568.11 318/568.1 318/590 395/95 901/7 901/9; and entitled: Method and System for Providing a Tactile Virtual Reality and Manipulator Defining an Interface Device Therefore which, provides a tactile virtual reality to a user is presented. The position and orientation of the user is utilized to generate a virtual reality force field. Forces are in turn generated on the user as a function of this force field. A six-axis manipulator is presented for providing a user interface to such a system. This manipulator provides a unique kinematic structure with two constant force springs which provide gravity compensation so that the manipulator effectively floats.

U.S. Pat. No. 5,388,990; issued Feb. 14, 1995; assigned to UNITED STATES OF AMERICA, NATIONAL AERONAUTICS AND SPACE ADMINISTRATION; classified at USPTO classification 434/38 345/8 364/578 395/152 434/43 434/307R 434/372; and entitled: Virtual Reality Flight Control Display with Six-Degree-of-Freedom Controller and Spherical Orientation Overlay, teaches a virtual reality flight control system which displays to the pilot the image of a scene surrounding a vehicle or pod having six degrees of freedom of acceleration or velocity control by the pilot and traveling through inertial space. The image itself includes a superimposed figure providing the pilot with an instant reference of orientation consisting of superimposed sets of geometric figures whose relative orientations provide the pilot an instantaneous feel or sense of orientation changes with respect to some fixed coordinate system. They include a first set of geometric figures whose orientations are fixed to the pilot's vehicle and a second set of geometric figures whose orientations are fixed with respect to a fixed or interstellar coordinate system. The first set of figures is a first set of orthogonal great circles about the three orthogonal axes of the flight vehicle or pod and centered at and surrounding the pilot's head, while the second set of figures is a second set of orthogonal great circles about the three orthogonal axes of a fixed or interstellar coordinate system, also centered at and surrounding the pilot's head.

U.S. Pat. No. 5,388,059, issued Feb. 7, 1995; assigned to the UNIVERSITY OF MARYLAND; USPTO classification 364/559 364/516; entitled: Computer Vision System for Accurate Monitoring of Object Pose; teaches a sensing system for accurately monitoring the position and orientation of an object. At least Four (4) point light sources are mounted on the surface of the object. A single electronic camera captures images of the point light sources. Locations of these images are detected in each camera image, and a computer runs an iterative task using these locations to obtain accurate estimates of the pose of the object in a camera coordinate system at video rate. The object is held by an operator for cursor control, for interaction with virtual reality scenes on computer displays, or for remote interactive control of teleoperated mechanisms.

U.S. Pat. No. 5,373,857; issued Dec. 20, 1994; assigned to FORTE TECHNOLOGIES, INC.; USPTO classification 128/782; entitled Head Tracking Apparatus; teaches a low cost head tracker for a virtual reality head set for determining the orientation of the head set relative to the earth's magnetic field includes a magnetic sensor responsive to the earth's magnetic field, and disposed on the head set and arranged with respect to a vertical axis of rotation of the head set to produce a displacement signal relative to the angular displacement of the head set with respect to a calibration orientation relative to the earth's magnetic field, and a signal processor connected to the magnetic sensor, and responsive to the electrical displacement signal for producing an output signal proportional to the orientation of the head set relative to the calibration orientation.

U.S. Pat. No. 5,347,400; issued Sep. 13, 1994; USPTO classification 359/815 345/7 345/8 359/630 359/742 359/813; entitled: Optical System for Virtual Reality Helmet; provides an optical system for a virtual reality head mounted display with improved image quality, enlarged field of view, and enhanced adjustability. In one embodiment, the optical system comprises a housing coupled to the frame of the head mounted display, a pair of displays mounted to the housing each defining a visual plane, and first and second lenses mounted between each of the displays and the user's eyes. The lenses are mounted to the housing such that each lens is disposed at an angle of between One (1) degree, and Fifteen (15) degrees relative to the visual plane. The lenses are also mounted such that the interoptic distance between the lenses may be adjusted. The optical system also has a unique lens construction including a standard Fresnel lens mounted in parallel to a low-diffraction Fresnel lens, resulting in substantially reduced diffractive interference.

U.S. Pat. No. 5,310,349; issued May 10, 1994; assigned to JOSTENS LEARNING CORPORATION; USPTO classification 434/350 345/156 364/419.2 395/152 395/927 434/118 434/307R 434/365; entitled: Instructional Management System; teaches a virtual school user interface running on networked personal computers for providing administrative and instructional functions to users in a scholastic environment. A user selects among grouped system functions by accessing one of a plurality of rooms within a school representation displayed on a video screen, with the networked virtual reality presenting the user as a real-time entity within the virtual school so that the user can interact with other users and system elements. A learning path editor is also provided for allowing users to author student curriculum sequences using graphical icons. A guidance tutor is further provided for coaching a student by displaying a guidance message on the video screen when so indicated by an instructional context. A courseware scheduler is further provided for delivering specific courseware to specific computers during specific time periods. A system monitor is further provided for gathering information in real-time on the state of each computer.

U.S. Pat. No. 5,227,985, issued Jul. 13, 1993; assigned to the UNIVERSITY OF MARYLAND; USPTO classification 364/559 345/158 364/516; entitled: Computer Vision System for Position Monitoring in Three Dimensions Using Non-Coplanar Light Sources attached to a monitored object; teaches a sensing system for monitoring the position and orientation of a rigid object. At least 4 point light sources are mounted on the surface of the object in a noncoplanar arrangement. A single electronic camera captures images of the point light sources. Locations of the images of the light sources are detected in each video image, and a computer runs a task using these locations to obtain close approximations of the rotation matrix and translation vector of the object in a camera coordinate system at video rate. The object is held by an operator for three-dimensional cursor control and interaction with virtual reality scenes on computer displays, and for remote interactive control of teleoperated mechanisms.

U.S. Pat. No. 5,214,615; issued May 25, 1993; USPTO classification 367/128 367/907; entitled: Three-Dimensional Displacement of a Body With Computer Interface; provides a system for tracking the three-dimensional position of an object within a three-dimensional region by triangulation techniques to generate signals corresponding to such three-dimensional positions. The signals may be used to operate a variably operable system to create a virtual reality system. The triangulation means may comprise at least three ultrasound emitters cooperating with ultrasound receivers located on a body moving in the three-dimensional region.

U.S. Pat. No. 5,185,561; issued Feb. 25, 1993; assigned to DIGITAL EQUIPMENT CORPORATION; USPO classification: 318/432 345/156 434/45; entitled: Torque Motor as a Tactile Feedback Device in a Computer System; teaches a hand held, one dimensional, torque feedback device used to feel and manipulate computer generated visual information and associated torque forces. In the preferred embodiment, molecular bond data is manipulated in a virtual reality system. The device can also be used with a workstation generated display on a plurality of problems which generate torque.

U.S. Pat. No. 5,172,313; issued Dec. 15, 1992; USPTO classification 364/401 395/925; Computerized Management System; teaches a computing apparatus for an improved system that manages. The apparatus has computing machinery which includes a computer and an input/output device for two-way communication between the computer and an operator. The computer includes operating instructions for: (a) receiving information from an operator during a management emergence stage necessary for developing a plan in machine readable language including a daily virtual (equivalent) cost for an objective (task/service); (b) processing the plan through a management convergence stage for generating subdivisional plans for output to an operator and receiving performance information as feedback for reducing the objective to a reality; (c) processing the management information and feedback information obtained during the emergence and convergence stages through a proliferative stage for generating specifications and quantitative goals for a new version of the objective for processing through the emergence and convergence stages including: (1) analyzing and selectively removing those tasks which have exceeded planned or suspended task time; and (2) performing a system analysis routine for (I) determining the completion of a task required in a most recent series of tasks and directing performance of the next task in the series to avoid duplication; and (ii) calculating the scheduled time for the remaining tasks in the series.

U.S. Pat. No. 5,130,794; issued Jul. 14, 1992; USPTO classification: 348/39 348/383; entitled: Panoramic Display System; teaches a panoramic image based virtual reality display system which includes a panoramic optical assembly, preferably of substantially spherical coverage, feeding composite optical images to a light sensitive surface of a video camera for storage or further processing in image processing circuitry. Such image processing circuitry includes a special effects generator and image segment circuitry to divide a composite image into a plurality of image segments or sub-segments for display on individual displays of multiple video display assemblies. Such a multiple video display assembly preferably includes a closed structure having individual display units mounted in all viewable directions therein, with segments of the composite image displayed on respective display units to recreate the panoramic view gathered by the panoramic optical assembly. The image processing circuitry may also select a portion or portions of the composite image for display on one or two displays of a head mounted display unit.

Various applications of mental visualization are also well known in the prior art, as exemplified by the following references which were found pursuant to a search of the MEDLINE database at the Library of Congress (hereinafter referred to as "LOC"), all of which are incorporated herein by reference in their entireties:

In LOC record number 92196384, dated 1992; entitled: *The Use of Hypnosis with Cancer Patients*, A. A. Levitan of the University of Minnesota, disclosed that mental visualization through hypnosis has been proven extremely valuable in the treatment of cancer patients. Specific applications include: establishing rapport between the patient and members of the medical health team; control of pain with self-regulation of pain perception through the use of glove anesthesia, time distortion, amnesia, transference of pain to a different body part, or dissociation of the painful part from the rest of the body; controlling symptoms, such as, nausea, anticipatory emesis, learned food aversions, etc.; psychotherapy for anxiety, depression, guilt, anger, hostility, frustration, isolation, and a diminished sense of self-esteem; visualization for health improvement; and dealing with death anxiety and other related issues. Hypnosis as a means of inducing mental visualization, has unique advantages for patients including improvement of self-esteem, involvement in self-care, return of locus of control, lack of unpleasant side effects, and continued efficacy despite continue use.

In LOC record number 95232172, dated February, 1995; entitled: *Effect of Imaging and Actual Tasting a Sour Taste on One Side of the Tongue*, P. D. Drummond of the Division of Psychology, Murdoch University, at Perth, Western Australia, disclosed the following experiment: to determine whether mental images can stimulate brainstem reflexes directly, parotid salivation was measured bilaterally in Twenty-Four (24) subjects when they imagined, and actually tasted, a sour taste on one side of the tongue. Salivation increased in both cheeks during unilateral gustatory stimulation; furthermore, the response was greater on the stimulated side than contra laterally, indicating that the gustatory reflex has a unilateral component. Subjects imagined the sour taste more clearly after actually experiencing it. However, salivation did not increase significantly during imagery trials, either before or after exposure to the sour taste. In fact, salivation to imagery decreased below baseline after exposure. These findings suggest that extraneous factors, i.e., the emotional connotation of mental images, anxiety, discomfort, repetitive measurement or fatigue, might sometimes inhibit specific reflex activity induced by metal images.

In LOC record number 95189392; dated October, 1994; entitled *Mental Practice of Motor Skills Used in Poststroke Rehabilitation Has Own Effects on Central Nervous System Activation*, T. Weiss, et al, of Friedrich Schiller University, Institute of Physiology, Jena, FR Germany, disclosed that in the last few years, it has been shown that the use of EMG triggered electrical myostimulation (ETEM) brings good results in poststroke rehabilitation. It has been hypothesized that the relearning effects obtained by means of ETEM are due to the reinstatement of proprioceptive feedback. However the technique is most powerful if imagination of motor acts, i.e., so-called "mental practice," is used as an initial part of ETEM. Since mental practice in healthy people leads to central nervous activation processes as well as to an improvement of motor skills, the authors investigated the effects of metal practice alone on central nervous activity by means of EEG in stroke patients. Twelve left-sided hemiplegic patients who underwent a specific poststroke rehabilitation treatment were requested to perform a simple arm movement sequence. In the following mental practice period, the patients were requested to imagine the same sequence without any real movement. EEG background activity was recorded during baseline and imagination periods. After the calculation of z-transformed power values within the alpha and beta-1 band, differences between rest and imagination periods were evaluated for significance. Stroke patients demonstrated significant decreases of alpha as well as beta-1 power during metal practice in comparison to the rest period. These changes are similar to those obtained in healthy subjects. Central alpha power diminished only during imagination of the contralateral arm. This phenomenon, as well as the decrease of beta-1 power in central derivation. were also obtained during real motor performance and might indicate an activation of the sensorimotor cortex. In accordance with the hypothesis of internal feedback mechanisms, this activation is a necessary prerequisite for motor learning during mental practice. The authors concluded that mental practice of motor skills might have its own effects on poststroke rehabilitation.

In LOC record number 95202933; dated February, 1995; entitled: *Neural Adaptation of Imaginary Visual Motion*, D. Gilden, et al, of The Department of Psychology, of the University of Texas at Austin, disclosed that observers made time-to-contact judgements about an imagined moving object that passed through an area of the visual field previously adapted to a single direction of real motion. The direction of imagined speed was slowed. When imagined motion was in the same direction as that experienced during adaptation, imagined speed slowed. When imagined speed was in the opposite direction, its speed increased. When adaptation and imagined motions were orthogonal, imagined speed was unaffected. The particular influence that prior adaptation has on imagined speed suggests that motion and real vision may engage common neural mechanisms without being functionally equivalent. Negative aftereffects observed in imagined motion imply that the imagination represents movement as an inference from position changes of static images.

In LOC record number 95049800; dated June, 1994; entitled: *Activation Process During Mental Practice in Stroke Patients*, T. Weiss, et al, of Friedrich Schiller University, Institute of Physiology, Jena, FR Germany, disclosed that mental practice is known to improve motor performance in health subjects. It is also known to be accompanied by a higher central nervous activity. Since such effects seem to be desirable for rehabilitation, the authors investigated the possibility of detecting changes in central nervous activity by means of EEG in stroke patients, and whether these changes were similar to those observed in healthy subjects. Twelve left-sided hemiplegic patients who underwent a specific post-stroke rehabilitation treatment were requested to perform a simple arm movement sequence. In the following mental practice period, the patients were requested to image the same sequence without any real movement. EEG background activity was recorded during rest and imagination periods. After the calculation of the z-transformed power values within the theta, alpha and beta-1 band, differences between rest and imagination periods were evaluated for their significance. Stroke patients show significant decreases of theta, alpha, as well as beta-1 power during metal practice in comparison to the rest period. These changes are similar to those obtained in healthy patients. Theta power decreases in central and parietal leads. Central alpha power diminishes only during imagination of the contralateral arm. this phenomenon, as well as the decrease of beta-1 power in central deviation were also obtained during real motor performance and might indicate an activation of the sensorimotor cortex. In accordance with the hypothesis of internal feedback mechanisms, this activation is a necessary prerequisite for motor learning during mental practice.

In LOC record number 94353191; dated 1994; entitled: *Hypnosis and the Allergic Response*, J. Wyler-Harper, et al, disclosed that in recent years our knowledge of the immune system and the pathogenesis of immune disorders has increased. There has been much research on the complex connections between the psyche, the central nervous system and the immune system and the effect of mood on disease processes. Their paper reviewed the evidence on the effects of hypnosis on the allergic skin test reaction, on allergies, particularly respiratory allergies and hayfever, and on bronchial hyperactivity and asthma. Hypnosis, which is generally regarded as an altered state of consciousness associated with concentration, relaxation and imagination and amongst other characteristics, an enhanced responsiveness to suggestion, has long been thought to be effective in the amelioration of various bodily disorders. It has seemed that the state of hypnosis is capable of a bridging or mediating function in the supposed dualism between mind and body. There has been great variation in the experimental and clinical procedures such as type of hypnotic intervention employed, the training of subjects and the timing of the intervention. Also, variability in the type of allergen used and its mode of application is evident. But despite these limitations, many of the studies have shown a link between the use of hypnosis and a changed response to an allergic stimulus or to a lessened bronchial hyperactivity. There is yet no clear explanation for the effectiveness of hypnosis, but there is some evidence for an influence on the neurovascular component of the allergic response.

Although virtual reality has been applied to the science of medicine, the literature is sketchy as to the limit and manner of its application, as exemplified by the following references which were found pursuant to a search of the MEDLINE database at the Library of Congress (hereinafter referred to as "LOC"), all of which are incorporated herein by reference in their entireties:

In LOC record number 94171544; dated December, 1993; entitled: *Virtual Reality: Applications in Medicine and Psychiatry*, E. Camare, of the Department of Psychiatry, John A Burns School of Medicine, University of Hawaii, disclosed that virtual reality is a coined description of a new computer-based technology that allows the user to enter a 3-D artificial world. Inside this world, the user can look around, move around and interact within computer worlds. The user can fly, visit exotic lands, play with molecules, "enter" cardiac chambers and watch blood swirl or do simulated surgery.

In LOC record number 95208929; dated April 1995; entitled: *Effectiveness of Computer-Generated (Virtual Reality) Graded Exposure in the Treatment of Acrophobia*, B. O. Rothbaum, et al, disclose a clinical trial, the goal of which was to examine the efficacy of computer-generated (virtual reality) graded exposure in the treatment of acrophobia (fear of heights). The authors concluded that treatment with virtual reality graded exposure was successful in reducing fear of heights.

In LOC record number 95111597; dated August, 1994; entitled: *Augmenting Reality in Rehabilitation Medicine*, W. J. Greenleaf, of Greenleaf Medical Systems of Palo Alto, Calif., disclosed some potential uses of virtual reality technology to support and augment routine activities for people who have physical disabilities.

In LOC record number 95111600; dated August, 1994; entitled: *A Resource Guide to VR in Medicine*, T. Emerson, et al, of the Human Interface Technology Laboratory of the University of Washington, Seattle, Wash., provided a bibliography of many of the most noteworthy contributions to the emerging literature about virtual reality in medicine. In LOC record number 94360023; dated May–June, 1994; entitled: *The Technique of Virtual Reality: a New Tool in Research of The Productive Symptoms in Psychiatry*, I. Zyss, presented the possibilities of the new computer technique of "virtual reality." It causes a nearly perfect "deception" of the central nervous function of the realizing judgement and can be a tool in research among others into the perception and its disturbances, especially into the productive symptoms in psychiatry.

In LOC record number 94191890; dated April, 1993; entitled: *Motor Skill Learning in Cerebral Palsy: Movement, Action and Computer-Enhanced Therapy*, J. P. Wann, et al of the Department of Psychology, of the University of Edinburgh, U.K., disclosed the extent to which previous research into movement control can provide key principles on which to model therapy for individuals with severe cerebral palsy. It is suggested that the movement perspective has traditionally stressed the role of implicit knowledge of the dynamic characteristics of the body and that this provides support for the principles of biofeedback training.

The terms "metaphor," and its variants as used herein is best defined by the following references which was found pursuant to a search of the MEDLINE database at the Library of Congress (hereinafter referred to as "LOC"), the entirety of which is incorporated herein by reference:

In LOC record number 94262584; dated April, 1994; entitled: *Interacting with Metaphors*, S. S. Kingsbury, of the Harvard Medical School, disclosed that creating metaphorical settings in which a patient may therapeutically interact while hypnotized would appear to have many of the advantages of more traditional uses of metaphors and to possess advantages of its own. Although this type of guided imagery may be widely used in practice, it is under-represented in the literature compared to other uses of metaphor. The author describes the use of a castle setting as one example of this type of metaphorical setting that may be useful in working with trauma patients.

In LOC record number 94038054; dated June, 1993; entitled: Healing and the Invention of *Metaphor: the Effectiveness of Symbols Revisited*, L. J. Kirmayer, of the Division of Social & Transcultural Psychiatry, McGill University, Montreal, Quebec, argued that a theory of meaning adequate to account for the effectiveness of symbolic healing and psychotherapy requires some variant of the three concepts of myth, metaphor and archetype. Myth stands for the overarching narrative structures of the self produced and lent authority by cultural tradition. Archetype stands not for performed ideas or images, but for the bodily-given in meaning. Metaphor occupies an intermediate realm, linking narrative and bodily-given experience through imaginative constructions and enactments that allow movement in sensory-affective quality space. This pluralistic perspective itself constitutes a middle-ground between constructivist and realist approaches to meaning that can integrate causal and interpretive models of symbolic healing.

Visual Subliminal Stimul

As evidenced, for example, by U.S. Pat. No. 3,060,795, issued Oct. 30, 1962 to R. E. Corrigan et al., and an article entitled "Perception of Subliminal Visual Stimuli" by A. C. Wlliams in Journal of Psychology, Vol. 6, July–October, 1938, it has long been known that indirect visual stimulation can reach through such mental blocks. However, the techniques of that patent involving subliminal perception rely upon an obscure and vague image that is difficult to perceive by many minds and subjects. That teaching is limited to producing a covert message with an effective intensity barely perceivable and below that ability or conscious recognition level of an observer to report the stimulus verbally. Thus, the message is presented in an environment where the observer is not consciously aware of any change in his environment and physical status when the input information is imparted.

This is an additional deficiency in the conditioning of, for example, psychological or psychic disorders. This is true because it is rarely possible to significantly improve behavior patterns unless the subject is willing to accept treatment from the therapist by self determination and has an interest in the correction of a problem. Corrigan further disclosed that a departure from those prior art teachings is thus necessary, both for obtaining a more prominent, intense and effective stimulus, and for treating subjects under environmental conditions where they are willing to look for solution to a problem. The primary object of Corrigan's invention is to provide more effective equipment for visual stimulation of a character useful for therapeutic treatment of psychological and psychic disorders. To that end, a covert message is placed in the environment of an overt message in such a way it can be subliminally displayed. Thus the message may be implanted into the observer's subconscious mind so that it will later materialize in a more acceptable form for inciting the observer's action and interest, namely as an apparent self derived observation from the observer's own recall and thinking process. By way of example, for therapeutic treatment of psychological and psychic disorders the message is made more effective and more forceful with more prominent reinforcement than feasible heretofore by a mode of operation in which the observer wants to be conditioned and is receptive to solution of a problem. Thus, although the subject knows he is undergoing subliminal conditioning he is not made conscious of the exact message which is being subliminally displayed or the nature of the subliminal conditioning. In this environment therefore a message is flashed periodically at an intensity so high that it overloads the observer's eye mechanism leaving an afterglow in the persistence medium much as occurs when a photo flash lamp is observed. The observer has only the message before him as by observation in a dark room. In this invention such a flashed message is readable by the observer but it is modulated by a covert message to thereby effectuate a stronger stimulus of a specific covert message than heretofore feasible with less intense messages applied in more detracting surroundings. The flash lamp or equivalent energy source for this visual stimulus mode is periodically triggered at a rate in the order of about one to three seconds between flashes to reinforce the conscious and subconscious images so formed thereby to induce an implanted message quickly and completely in the memory banks of the observer for his later recall as a new and refreshing thought derived by his own thinking, analysis and discovery.

U.S. Pat. No. 4,279,088 to Hyre, disclosed a simple instrument for effecting conditioning phenomenon. It embodied a viewing plane for holding a written or printed message in viewing position. This could be simply a glass plate for receiving one or two paper sheets. The paper which is partially opaque is made translucent when passing the high intensity light photo flash therethrough, thus permitting an overt message on the face or back of the paper sheet to be viewed and read by the observer. Then a second covert message on a second paper sheet or the back of a first in less prominent contrast also is presented in subliminal form by flashing the light source of high intensity such as a gaseous discharge tube. The high intensity flash is much shorter than the persistence period of the eye mechanism being a small fraction of a second, and therefore with the lesser contrast of the covert message does not permit the viewer to consciously read the covert message. However, possibly because of the high intensity causing the afterglow effect, the covert message is available in the eye mechanism for inciting the brain channels which stores the message for later recall, and very effectively implants the message for later use by the observer. This leads to the introduction of suggestions in conditioning that would be otherwise rejected and contested if directly introduced by the operator and converts the message by subliminal implantation into a suggestion more readily followed by a subject who deems it to be by his own reasoning.

In yet another U.S. Pat. No. 4,270,284 to Skellings; the object of that invention is to provide a colored text display of language to metaphorically identify (implied comparison) heretofore subliminal patterns of linguistic, literary, and/or stylistic features of languages. In his examples, Skellings discloses text display examples that are used to teach linguistic, literary, and/or stylistic features of languages. The display includes in a single frame text language in which at least two portions of the text language are emphasized by similar or identical colors that are different from the color of the text language or the background. As used therein, the word color includes black. The color emphasis may be accomplished by coloring the indicia such as a letter or emphasis mark, aura, or outline around a letter or emphasis mark, block, or plurality of blocks around indicia, or background portions of the display portions. This display may be utilized for better and. faster teaching of features of languages by metaphorically identifying (color comparing) heretofore subliminal patterns in the minds of a subject. It is well known that many subjects fixate on letters and/or words in language text and consciously block out all other intellectual consciousness of the language text previously read. This new and improved display cuts through the veil of subliminal consciousness or brings forth for comparison by highlighting the internal linguistic, literary, and/or stylistic features of languages. The color emphasis aids recognition, absorption, and retention as well as providing a better comparison teaching aid. The teaching system or method is to create and visually display in a single frame text languages with portions such as indicia, words, grammar, syntax, meter, rhyme, and/or poetic devices (prosody) emphasized by color assignments to indicia, aura around indicia, blocks around indicia and background portions to teach linguistics, literary, and/or stylistic features of those languages in order to metaphorically identify heretofore subliminal patterns within such text languages. To more specifically illustrate his invention, Skelling set forth the following one of a number of examples; in the language text:

> PETER PIPER PICKED A PECK OF PICKLED PEPPERS A PECK OF PICKLED PEPPERS DID PETER PIPER PICK IF PETER PIPER PICKED A PECK OF PICKLED PEPPERS HOW MANY PICKLED PEPPERS DID PETER PIPER PICK?

In the first line, the alliteration may be emphasized by red letters on indicia and the related consonance may be emphasized by violet letter. Therefore, in the first line, the letters in red are the P in PETER, the P in PIPER, the P in PICKED, the P in PECK, the P in PICKLED, and the P in PEPPERS. The related consonance in the first line the letters in violet are the second P in PIPER, and the second and third P's in PEPPERS. The internal rhyme may be emphasized by yellow letters. Therefore, the ER in PETER, the ER in PIPER, and the ER in PEPPERS. Unrelated consonance may be emphasized in light blue letters. Therefore, the CK in PICKED, and the CK in PECK would be light blue. The sound of speech in all good poems is patterned carefully as this.

Various prior art inventions have disclosed various types of apparatus for perfecting subliminal conditioning. For example U.S. Pat. No. 5,027,208 to Dwyer, et al, relates to systems for generating subliminal messages synchronously added to selected supraliminal messages where the combined image is displayed for the purpose of therapeutically influencing behavior.

The behavior of individuals may be influenced by visual messages generated at intensity or duration levels sufficiently low that they are not consciously perceived. A variety of systems have been developed to display a supraliminally perceptible visual image having a subliminally perceptible message presented in conjunction therewith. These systems typically use motion picture or television systems for displaying conventional programs along with a therapeutic message that is not consciously perceptible by a human observer but is capable of influencing the subconscious mind of the observer in such a way as to influence behavior.

The systems typically involve arrangements wherein both the source of the supraliminal video signal and subliminal video signal are under the control of the system's operator. In a motion picture version, a pair of separate motion picture projectors employ a mechanism connecting them so that they operate in synchrony to generate the supraliminal program signal along with the superimposed subliminal message. Alternatively, pairs of television cameras have been used to separately generate two signals which are synchronized to provide a combined signal suitable for use with a television receiver.

The apparatus required for most existing systems has severely limited their application. However, some subliminal message systems have utilized readily available equipment and conventionally broadcast programs for the supraliminal program source and simply switch to a subliminal signal at short intervals to impress the observer with a subliminal message that might direct the observer to undertake desirable action.

More specifically, the Dwyer invention relates to portable systems for implementing behavior modification therapy wherein a subliminal message is added to a preexisting supraliminal message and the combined image is displayed on a video screen. A television receiver or video recorder can be used to provide the supraliminal message. The desired subliminal message or image is provided by a preprogrammed chip that is inserted by the user into a compact video processing circuit that combines the two signals for viewing. The video processing system synchronizes the video signal containing the supraliminal message with a signal containing the desired subliminal message. The system then either lightens or darkens portions of the supraliminal message, in a manner that is not consciously perceptible to the viewer, to present the subliminal message. Thus an optical characteristic of a portion of the supraliminal message is altered slightly to incorporate the subliminal message. An analog oscillator is used in conjunction with a digital circuit to synchronize the subliminal message signal with the existing video signal. A video synchronization detector circuit receives the supraliminal video signal and generates digital outputs that mark the beginning of each vertical and horizontal line within the two dimensional image. These vertical and horizontal synchronization signals are used to instruct a microprocessor, which accesses a digital memory in which the subliminal message has been stored, to deliver the contents of each line of the subliminal message for addition to the appropriate line of the supraliminal image. An analog oscillator is used rather than a crystal clock because it can be stopped by a composite synchronization pulse and re-started, thereby starting each line at exactly the same time interval following the synchronization pulse. This results in improved stability of the subliminal message relative to the supraliminal message during one scan of the screen and between successive scans. A monostable ("one shot") multivibrator is gated by the microprocessor to produce pulses so that only selected portions of each supraliminal image are altered to incorporate the subliminal message. The oscillator is controlled directly by the one-shot's output and is stopped only for the duration of the one-shot pulse. A counter is used to control delivery of the subliminal message for each screen line. The counter does not depend on the stopping of the oscillator to control counting. Rather, the counter disables itself after counting the pixels on each line of the subliminal image and allows the oscillator to run. The one-shot is used to both stop the oscillator and zero the counter. This video mixer thus uses a simple control circuit to provide placement of the subliminal message anywhere on the supraliminal image. The system avoids the use of noisy analog differentiation circuits to provide pulse signals which control circuit operation.

Audible Subliminal Stimuli

The techniques of training or teaching through the use of subliminal audio signals is also well known, as presented, for example, in U.S. Pat. No. 3,060,795 to Corrigan and U.S. Pat. No. 3,278,676 to Becker. In such methodology an audio recording, typically on audiotape, is prepared with a recording of a desired spoken message at a first, low volume. This is the subliminal message signal. A second audio signal, typically music, is also impressed on the recording medium at a second, higher amplitude. The second signal masks the first such that the first cannot be perceived by the listener upon playback. The theory of subliminal perception states that while the first, subliminal signal cannot be perceived in the normal manner, its existence on the recording medium and playback at a subliminal level results in the unconscious receipt of the signal and a corresponding effect upon the listener. Depending on the content of the subliminally recorded message, such recordings have been used for a variety of training regimens, such as weight control, smoking cessation, memory development, and the like. Because a subliminal recording, by definition, includes a message signal which is not intended to be consciously perceived by the listener in the normal manner, the listener is not likely to be consciously "aware" of the existence of a subliminal message in a recording. Despite some questions as to the actual effect of such signals, prohibitions exist against the use of such material in certain situations, such 1is as in broadcast advertisements, to guard against the presentation of such material to those not consenting to its use. On the other hand, the user of a subliminal recording has the vital concern that the intended subliminal message is in fact there. The user, having invested in the recording, properly has the interest that, for example, the stop-smoking tape he purchased does indeed have a motivation message to assist him or her in his quest. In addition, the user may wish to be assured that the content of the subliminal track is acceptable, and does not contain material which he or she would find objectionable or improper for the intended purpose. Since the very essence of a subliminal recording is that the subliminal message cannot be perceived normally, that quality serves as a bar to verification of its existence. Other than at the master recording level, where the subliminal and supraliminal mask signals are blended together and thus can be identified, it's extremely difficult to confirm the existence of a subliminal message signal on a recording. This leaves the recording manufacturer with the risk of claims that the subliminal message is non-existent or other than what it is alleged to be, and places the user of the recording in the uncomfortable position of being unable to verify the legitimacy and suitability of the product he has obtained.

U.S. Pat. No. 5,224,864 to Vavagiakis discloses an audio recording and a method of making same in which the recording has a subliminal message signal and a masking signal mixed together. A stereophonic or two track recording process is utilized, in which a monaural masking signal is placed on both tracks in an in-phase relationship. A monaural subliminal message is also placed on both tracks, but in a 180° inverted phase relationship between the tracks. The masking signal and the subliminal message signal for each track are combined in the normal manner for a subliminal recording, the relative amplitudes of the signals being chosen such that the subliminal signal is masked by the other signal. The resulting recording can be used in the conventional manner on stereophonic or monaural playback equipment. To verify the existence of the subliminal message signal, the signals on the two tracks are combined in a 180° deg. relative phase relationship. Because the masking signals on the two tracks were recorded in phase, the inversion places them in a canceling relationship, such that the masking signal cannot be heard. The subliminal message signals, on the other hand, being recorded in an out-of-phase relation, are placed in phase by the conversion, such that the signals are combined and become audible. Thus the listener hears only the subliminal message signal and can confirm the existence of the normally-inaudible message. A further benefit of the present invention is that the subliminal message can be recorded at a higher amplitude, the out-of-phase relationship between the left and right channel signals on two track playback providing a further deadening effect to conscious perception of the message.

Notwithstanding the foregoing, there is no teaching in the prior art of any means and/or method for perfecting the skill of mental visualization in the mind of a subject through the use of virtual reality combined with subliminal stimuli. Thus, there exists a long felt need for such a means and/or method.

It is therefore the primary object of the instant invention to satisfy these long felt need.

SUMMARY OF THE INVENTION

The instant invention provides an article of manufacture comprising a medium with a computer program printed thereon, operable within a virtual reality device which is designed for perfecting mental visualization within the mind of a subject sufficient alone to effect a desired neurological and/or physiological change within the body of said subject, even in the substantial absence of any physical movement by the subject. The program includes a dynamic scenario that is designed to communicate in chronological order: (i.) a condition which requires a remedy; (ii.) a mode for effecting the remedy; (iii.) the performance of the mode so as to effect the remedy; and, (iv.) rectification of the condition through the performance of the mode. The program is interspersed with audible, visual or combined audible/visual subliminal stimuli, designed to aid a subject in achieving the goal. It also provides the program medium in combination with a virtual reality device and a method of using the same. The steps of the method include: operatively interfacing the program medium with the device and mounting the device on the subject; and, running the program. (Note here that the mounting step may proceed the interfacing step). The program is designed to communicate a dynamic real or metaphoric, or combination of real and metaphoric scenario to the subject which is designed for perfecting mental visualization within the mind of the subject sufficient alone to effect a desired neurological and/or physiological change within the body of the subject, even in the substantial absence of any physical movement by the subject. Optionally, it can also be further designed to effect preconditioning of the subject's mind, such as inducing a state of meditation or hypnosis, or a combination thereof The scenario of the program can be designed to exist in real time, real space, compressed time, compressed space, expanded time, expanded space, or any combination thereof. Optionally the program is further designed to enable (motor) interaction between the subject and/or an operator external to the preconditioning and the subject. Although the instant invention primarily contemplates visual stimulation and/or interaction with the subject, is also applicable to visual sense in combination with any one or more of the other senses of the subject.

More specifically, the present invention provides an article of manufacture for use with a virtual reality device that includes a medium with a program imprinted thereon. The medium is operable with the device and designed for presentation to at least the visual senses of a subject. The invention also contemplates sensory input to at least the other senses of a subject including at least the hearing and touch senses. The program includes: (a) a first optional portion for preconditioning the mind of the subject to a precondition receptive to a dynamic scenario; and, (b) the dynamic scenario. Subliminal messages are interspersed at preselect points throughout the program. These messages are visual, audible or, both visual and audible. These subliminal messages are designed in accord with the teachings of the prior art as disclosed herein. The dynamic scenario is designed to communicate in chronological order: (i.) a condition which requires a remedy; (ii.) a mode for effecting the remedy; (iii.) the performance of the mode so as to effect the remedy; and, (iv.) rectification of the condition through the performance of the mode. The program thereby effectively causes mental visualization within the mind of the subject sufficient to enable the subject to achieve the desired goal. The goal is physical learning, mental learning, physical training, mental training, physical healing, mental healing or any combinations thereof The invention also specifically contemplate a method of using the novel medium, that includes: mounting the virtual reality device on the subject; operably interfacing the medium with the device; and, running the program. The instant invention also contemplates the combination of the article and a virtual reality device.

More specifically, the present invention provides an article of manufacture for use with a virtual reality device that includes a medium with a program imprinted thereon. The medium is operable with the device and designed for presentation to at least the visual senses of a subject. The invention also contemplates sensory input to at least the other senses of a subject including at least the hearing and touch senses. The program includes: (a) optionally, a portion for preconditioning the mind of the subject to a precondition receptive to a dynamic scenario; and, (b) the dynamic scenario. Subliminal messages are interspersed at preselect points throughout the program. These messages are visual, audible or, both visual and audible. These subliminal messages are designed in accord with the teachings of the prior art as disclosed herein. The dynamic scenario communicates in chronological order: (i.) a condition which requires a remedy; (ii.) a mode for effecting the remedy; (iii.) the performance of the mode so as to effect the remedy; and, (iv.) rectification of the condition through the performance of the mode. In addition, the program is interspersed with audible, visual or combined audible/visual subliminal stimuli, designed to aid a subject in achieving the goal. The program thereby effectively causes mental visualization within the mind of the subject sufficient to enable the subject to achieve the desired goal. The goal is physical learning, mental learning, physical training, mental training, physical healing, mental healing or any combinations thereof. The invention also specifically contemplate a method of using the novel medium, that includes: mounting the virtual reality device on the subject; operably interfacing the medium with the device; and, running the program. The instant invention also contemplates the combination of the article and a virtual reality device.

Definitions as used Herein

The term "medium" as used herein is intended to denote any known physical article upon which a computer program may be imprinted, for subsequent transmission to a computer device, including but not limited to a floppy diskette, a tape, a computer hard drive or any other such known computer medium. Here a floppy disk is preferred.

The terms "imprint" and its variants as used herein, is intended to denote any known means by which information is imparted to computer medium, for subsequent transmission to a computer device. Here electronic imprinting of the computer medium is preferred.

The term "interaction" and its variants as used herein, is intended to denote the process by which a subject contributes motor/sensory response to some stimulus provided by the virtual reality program, as well as the response generated through the program in answer to the subject's motor/sensory response.

The term "altered mental state(s)" as used herein, is intended to denote any mental state of a subject other than, his normal waken state.

The term "body of a subject" as used herein, refers to any portion of the body of the subject wherein a change including but not limited to a physiological change, a neurological and combinations thereof, occurs that is consistent with the goals in the practice of the invention, including but not limited to: physical learning, mental learning, physical training, mental training, physical healing, mental healing and combinations thereof.

DETAILED DESCRIPTION OF THE INVENTION

The instant invention can best be described in detail by the following examples:

EXAMPLE 1

A subject has intense pain in his left hand. The pain is treated, by mounting a virtual reality apparatus on the subject. The apparatus is interfaced with a medium having a computer program imprinted thereon. The program is interspersed with subliminal stimuli. These subliminal stimuli are audible and/or visual, and are designed and spaced within the program to maximally aid in effecting the goal of reducing the pain in left hand of the subject. A first optional portion of the program is designed in time and content for perfecting, a state of meditation and/or hypnosis in the mind of the subject by any one of a multitude of well known prior art techniques. The technique is delivered to the subject by plural sensory representation by the program through the apparatus. After the desired altered mental state of the subject is achieved, a second portion of the program is run. This portion of the program provides the subject with a multisensory depiction of a dynamic metaphoric scenario designed to merely augment or completely supplant the subject's ability to control the pain in his hand through mental visualization. The metaphoric scenario depicts, for instance, the inside of a control room, symbolizing the subject's brain. The control room contains a panel having a plurality of conduits leading from it. Each conduit is provided with a label and a switch connected in series with an alarm and/or light, each symbolizing a neural conduit. One of the labels reads: "left hand," symbolizing that this is the nerve leading to the left hand. The word "ouch" is subliminally visually flashed around the sign and/or subliminally audibly interspersed into the program when the subject's attentions are directed to the sign. Alternately to the word "ouch !" symbols, such as, i.e., radiating lightening bolts can replace or be added to the word as the subliminal stimuli. In order to relieve the pain in his left hand, the subject interacts with the apparatus and program by turning off the switch labeled "left hand." When the switch is turned off, the "ouch !" is replaced with a visual and/or audible "ahhh !" subliminal stimulus, thereby symbolizing that the pain has been relieved. As noted above, the "ahhh !" can be replaced or augmented with an appropriate symbol. Optionally interaction can be effected by an operator other than the subject. The scenario is designed to play out in real time, real space, compressed time, compressed space, expanded time, expanded space and combinations thereof. Alternatively, the subliminal stimuli may be effected by the operator. The foregoing process is repeated according to a prescribed regimen, until the subject is able to achieve effective unaided mental visualization.

EXAMPLE 2

A subject desires to improve his technique at the high jump. Mental training is effected, by mounting a virtual reality apparatus on the subject. The apparatus is interfaced with a medium having a computer program imprinted thereon. The program is interspersed with subliminal stimuli. These subliminal stimuli are audible and/or visual, and are designed and spaced within the program to maximally aid in effecting the goal of improving the high jump technique of the subject. A first optional portion of the program is designed in time and content for perfecting, a state of meditation and/or hypnosis in the mind of the athlete by any one of a multitude of well known prior art techniques. The technique is delivered to the athlete by plural sensory representation through the apparatus. After the desired altered mental state of the athlete is achieved, a second portion of the program is run. This portion of the program provides the athlete with a multisensory depiction of a dynamic scenario designed to merely augment or completely supplant the athlete's ability to practice the high jump through mental visualization. The scenario depicts a substantially real particle world depiction of a/the athlete performing a high jump. The athlete interacts with the apparatus and program to perfect his jump. The "thumbs up" symbol is subliminally visually communicated to the athlete through the scenario when the athlete successfully perfects his jump in accordance with predetermined parameters embodied in the program. In this manner, the behavior that proximately results in the successful completion of the goal is affirmed. Conversely, the "thumbs down" symbol is visually communicated to the athlete through the scenario when the athlete interacts in some manner that causes unsuccessful completion of the goal. Alternately to the symbols, respective word phrases such as "all right!" and "too bad, try again" can replace or be added to the respective symbols as the subliminal stimuli. Optionally, interaction can also be effected by a coach. Thus, the subliminal stimuli may also be effected by the coach. The foregoing process is repeated according to a prescribed regimen, until the athlete is able to achieve mental visualization sufficient for effective mental practice. In this manner the desired neurological and/or physiological changes normally incidental to physical practice can be achieved in the substantial absence of such physical practice.

EXAMPLE 3

A subject suffers from a blood borne disease such a leukemia. The disease is treated, by mounting a virtual reality apparatus on the subject. The apparatus is interfaced with a medium having a computer program imprinted thereon. The program is interspersed with subliminal stimuli. These subliminal stimuli are audible and/or visual, and are designed and spaced within the program to maximally aid in effecting the goal of curing the leukemia of the subject. A first optional portion of the program is designed in time and content for perfecting, a state of meditation and/or hypnosis in the mind of the subject by any one of a multitude of well known prior art techniques. The technique is delivered to the subject by plural sensory representation through the apparatus. After the desired altered mental state of the subject is achieved, a second portion of the program is run. This portion of the program provides the subject with a multisensory depiction of a dynamic metaphoric scenario designed to merely augment or completely supplant the subject's ability to reduce cancer cells in his blood through his natural physiological mechanisms perfected through mental visualization. The scenario depicts, for instance, a coral reef in a lagoon, symbolizing the interior of the subject's circulatory system. A school of small black fish symbolizing cancer cells, are nibbling away at the coral reef. The word "danger !" is subliminally visually flashed around the sign and/or subliminally audibly interspersed into the program when the subject's attentions are directed to the sign. Alternately to the word "danger !" symbols, such as, i.e., a skull and cross-bones can replace or be added to the word as the subliminal stimuli. Another school of large white fish, symbolizing antibodies, enters the scene, and begins to devour the school of black fish. The phrase "here comes the calvary !" is subliminally visually caused to appear to the subject through the scenario so as to signify that help is on the way. Alternately to the phrase "here comes the calvary!" a appropriate symbols, such as, i.e., a still picture of a charging calvary, can replace or be added to the phrase as the subliminal stimuli. Optionally interaction can be effected by an operator other than the subject. Alternatively, the subliminal stimuli may be effected by the operator. The scenario is designed to play out in real time, real space, compressed time, compressed space, expanded time, expanded space and combinations thereof. The foregoing process is repeated according to a prescribed regimen, until the subject is able to achieve effective mental visualization.

EXAMPLE 4

A subject desires to improve his technique at a skating routine. Mental training is effected, by mounting a virtual reality apparatus on the subject. The apparatus is interfaced with a medium having a computer program imprinted thereon. The program is interspersed with subliminal stimuli. These subliminal stimuli are audible and/or visual, and are designed and spaced within the program to maximally aid in effecting the goal of improving the skating technique of the subject. A first optional portion of the program is designed in time and content for perfecting, a state of meditation and/or hypnosis in the mind of the skater by any one of a multitude of well known prior art techniques. The technique is delivered to the skater by plural sensory representation through the apparatus. After the desired altered mental state of the skater is achieved, a second portion of the program is run. This portion of the program provides the skater with a multisensory depiction of dynamic scenario designed to merely augment or completely supplant the skater's ability to practice the skating routine through mental visualization. The scenario depicts a substantially real particle world depiction of a/the skater performing the desired routine. The skater interacts with the apparatus and program to perfect the routine. The "thumbs up" symbol is subliminally visually communicated to the athlete through the scenario when the athlete successfully perfects his jump in accordance with predetermined parameters embodied in the program. In this manner, the behavior that proximately results in the successful completion of the goal is affirmed. Conversely, the "thumbs down" symbol is visually communicated to the athlete through the scenario when the athlete interacts in some manner that causes unsuccessful completion of the goal. Alternately to the symbols, respective word phrases such as "all right !" and "too bad, try again" can replace or be added to the respective symbols as the subliminal stimuli. Optionally, interaction can also be effected by a coach. The foregoing process is repeated according to a prescribed regimen, until the skater is able to achieve mental visualization sufficient for effective mental practice. Thus, the subliminal stimuli may also be effected by the coach. In this manner the desired neurological and/or physiological changes normally incidental to physical practice can be achieved in the substantial absence of such physical practice.

EXAMPLE 5

A subject suffers from a fractured leg. The condition is treated, by mounting a virtual reality apparatus on the subject. The apparatus is interfaced with a medium with a computer program imprinted thereon. The program is interspersed with subliminal stimuli. These subliminal stimuli are audible and/or visual, and are designed and spaced within the program to maximally aid in effecting the goal of healing the fractured leg of the subject. A first optional portion of the program is designed in time and content for perfecting, a state of meditation and/or hypnosis in the mind of the subject by any one of a multitude of well known prior art techniques. The technique is delivered to the subject by plural sensory representation through the apparatus. After the desired altered mental state of the subject is achieved, a second portion of the program is run. This portion of the program provides the subject with a multisensory depiction of a dynamic metaphoric scenario designed to merely augment or completely supplant the subject's ability to promote mending of the fractured bone through physiological mechanisms perfected through mental visualization. The scenario depicts, for instance, a bridge, a span of which has been damaged by an earthquake. A crew of workmen proceeds to reconstruct the span until it is restored, thereby symbolizing the physiological mechanism through which a bone fracture is mended. As taught above, the phrase "here comes the calvary !" is subliminally visually caused to appear to the subject through the scenario so as to signify that help is on the way. Alternately to the phrase "here comes the calvary!" a appropriate symbols, such as, i.e., a still picture of a charging calvary, can replace or be added to the phrase as the subliminal stimuli. Optionally interaction can be effected by an operator other than the subject. Alternatively, the subliminal stimuli may be effected by the operator. The scenario is designed to play out in real time, real space, compressed time, compressed space, expanded time, expanded space and combinations thereof. The foregoing process is repeated according to a prescribed regimen, until the subject is able to achieve effective mental visualization.

EXAMPLE 6

A subject suffers from a profound metal depression associated with low self-esteem. The condition is treated, by mounting a virtual reality apparatus on the subject. The apparatus is interfaced with a medium with a computer program imprinted thereon. The program is interspersed with subliminal stimuli. These subliminal stimuli are audible and/or visual, and are designed and spaced within the program to maximally aid in effecting the goal of improving the self-esteem and abating the depression of the subject. A first optional portion of the program is designed in time and content for perfecting, a state of meditation, hypnosis and/or altered mental states, in the mind of the subject by any one of a multitude of well known prior art techniques. The technique is delivered to the subject by plural sensory representation through the apparatus. After the desired altered mental state of the subject is achieved, a second portion of the program is run. This portion of the program provides the subject with a multisensory depiction of a dynamic metaphoric scenario designed to merely augment or completely supplant the subject's ability to dispel his profound depression through his own physiological mechanisms perfected through mental visualization. The scenario depicts, for instance, the Nobel prize ceremonies where the subject is about to receive the Nobel humanitarian prize. His acceptance is proceeded by a number of testimonial by others praising his finer qualities. The "thumbs up" symbol is subliminally visually communicated to the subject through the scenario at points therein that the subject is praised. In this manner, the improved self-esteem that proximately results in the successful completion of the goal is affirmed. Optionally interaction can be effected by an operator other than the subject. Thus, the subliminal stimuli may also be effected by the operator. The scenario is designed to play out in real time, real space, compressed time, compressed space, expanded time, expanded space and combinations thereof. The foregoing process is repeated according to a prescribed regimen, until the subject is able to achieve effective mental visualization.

EXAMPLE 7–10

The principles of foregoing Example 6 are equally applicable to the rectification of phobias, including, but not limited to: specific phobias, such as the fear of, i.e., dogs, snakes, spiders, mice, and the like; claustrophobia, such as the fear of, i.e., heights, air travel, elevators, and the like; agoraphobia, such as open spaces, entering public places, and the like; and, social phobia, as in fear of being exposed to the scrutiny of others, such as the fear of eating, speaking, or performing in public, using public toilets or writing in the presence of others.

EXAMPLE 11

A subject who has suffered a stroke desires to improve his control and movement over the paralyzed half of his body. Mental training is effected, by mounting a virtual reality apparatus on the subject. The program is interspersed with subliminal stimuli. These subliminal stimuli are audible and/or visual, and are designed and spaced within the program to maximally aid in effecting the goal of improving the subject's control and movement over the paralyzed half of his body. The apparatus is interfaced with a medium having a computer program imprinted thereon. A first optional portion of the program is designed in time and content for perfecting, a state of meditation and/or hypnosis in the mind of the subject by any one of a multitude of well known prior art techniques. The technique is delivered to the subject by plural sensory representation through the apparatus. After the desired altered mental state of the subject is achieved, a second portion of the program is run. This portion of the program provides the subject with a multisensory depiction of a dynamic scenario designed to merely augment or completely supplant the subject's ability to practice exercising his effected limbs through mental visualization. The scenario depicts a substantially real particle world depiction of a/the subject performing some physical task otherwise designed to rehabilitate the effected limbs. The "thumbs up" symbol is subliminally visually communicated to the subject through the scenario as the subject successfully progresses in using the effected limbs. In this manner, the behavior that proximately results in the successful completion of the goal is affirmed. The subject interacts with the apparatus and program to perfect his rehabilitation. Thus, the subliminal stimuli may also be effected by the operator. Optionally, interaction can also be effected by a medical care provider. The foregoing process is repeated according to a prescribed regimen, until the subject is able to achieve mental visualization sufficient for effective mental practice. In this manner the desired neurological and/or physiological changes normally incidental to physical practice can be achieved in the substantial absence of such physical practice.

EXAMPLE 12

A subject who smokes wishes to quit smoking. Mental training is effected, by mounting a virtual reality apparatus on the subject. The apparatus is interfaced with a medium having a computer program imprinted thereon. The program is interspersed with subliminal stimuli. These subliminal stimuli are audible and/or visual, and are designed and spaced within the program to maximally aid in effecting the goal of helping the subject to quit smoking. A first optional portion of the program is designed in time and content for perfecting, a state of meditation and/or hypnosis in the mind of the subject by any one of a multitude of well known prior art techniques. The technique is delivered to the subject by plural sensory representation through the apparatus. After the desired altered mental state of the subject is achieved, a second portion of the program is run. This portion of the program provides the subject with a multisensory depiction of a dynamic scenario designed to merely augment or completely supplant the subject's ability to discontinue the habit of smoking through mental visualization. The scenario can, for example, depict a substantially metaphoric depiction of the subject smoking a cigarette, wherein the cigarette begins to grow and appear to become more and more menacing, while the subject begins to shrink and appears more and more sickly. The word "danger !" is subliminally visually flashed around the sign and/or subliminally audibly interspersed into the program when the subject's attentions are directed to the sign. Alternately to the word "danger !" symbols, such as, i.e., a skull and cross-bones can replace or be added to the word as the subliminal stimuli. The scenario then changes. The subject withdraws the cigarette from his mouth throws it to the ground, signify that the tide of the battle of his addiction has turned. At this point, the "thumbs up" symbol is then subliminally visually communicated to the subject through the scenario. In this manner, the behavior that proximately results in the successful completion of the goal is affirmed. The subject interacts with the apparatus and program to perfect his rehabilitation from his addition to tobacco. Optionally, interaction can also be effected by an operator. Thus, the subliminal stimuli may also be effected by the coach. The foregoing process is repeated according to a prescribed regimen, until the subject is able to achieve mental visualization sufficient for effective mental practice. In this manner the desired neurological and/or physiological changes normally incidental to physical practice can be achieved in the substantial absence of such physical practice.

EXAMPLE 13–15

The principles of foregoing Example 12 are equally applicable to the rectification of other addictive behavior, such as, but not limited to: over eating, alcohol addition, drug addition.

Although the invention has been described with reference to certain preferred examples, it will be appreciated that many variations and modifications may be made within the scope of the broad principles of the invention. Hence, it is intended that the preferred examples and all of such variations and modifications be included within the scope and spirit of the invention, as defined by the following claims.

I claim:

1. A method comprising:
   providing a virtual reality device;
   providing a medium with a program imprinted thereon designed for achieving a goal desired by a subject, operable with the device for presenting to at least the visual senses of the subject; said program including:
   at one subliminal stimulus selected from the group of audible subliminal stimulus, visual subliminal stimulus and combinations thereof; and,
   a dynamic scenario, that is designed to communicate in chronological order:
   (I.) a condition which requires a remedy;
   (ii.) a mode for effecting the remedy;
   (iii.) the performance of the mode so as to effect the remedy; and,
   (iv.) rectification of the condition through the performance of the mode;
   for causing mental visualization within the mind of the subject sufficient to enable the subject to achieve the desired goal;
   wherein the goal is selected from the group consisting: of physical learning, mental learning, physical training, mental training, physical healing, mental healing and combinations thereof;
   operatively interfacing the medium with the device and mounting the device on the subject; and,
   running the program.

2. The method of claim 1, wherein said program is further designed to enable interaction between said subject and/or an external operator, and said device.

3. The method of claim 1, wherein said program is further designed to communicate a metaphoric or real, or combined real and metaphoric scenario to said subject designed for perfecting said mental visualization.

4. The method of claim 3, further comprising: effecting said precondition with said program.

5. The method of claim 4, wherein said precondition is one of the group consisting of: meditation, hypnosis, altered mental states, and combinations thereof, and is effected by said program.

6. The method of claim 6, wherein said scenario exists in one of the group consisting of: real time, real space, compressed time, compressed space, expanded time, expanded space and combinations thereof.

7. An article of manufacture for use with a virtual reality device comprising a medium with a program imprinted thereon operable with the device and designed for presenting to at least the visual senses of the subject; said program including:
   at one subliminal stimulus selected from the group of audible subliminal stimulus, visual subliminal stimulus and combinations thereof, and,
   a dynamic scenario, that is designed to communicate in chronological order:
   (I.) a condition which requires a remedy;
   (ii.) a mode for effecting the remedy;
   (iii.) the performance of the mode so as to effect the remedy; and,
   (iv.) rectification of the condition through the performance of the mode; for causing mental visualization within the mind of the subject sufficient to enable the subject to achieve the desired goal; wherein the goal is selected from the group consisting of: physical learning, mental learning, physical training, mental training, physical healing, mental healing and combinations thereof, when the device is mounted on the subject and the medium is operably interfaced with the device, and the program is caused to run.

8. The article of claim 7, wherein the program is further designed to enable interaction between the subject and/or an external operator, and the device.

9. The article of claim 8, wherein said program is further designed to communicate a metaphoric or real, or combined real and metaphoric, scenario to said subject designed for perfecting said mental visualization.

10. The article of claim 9, wherein said program is further designed to effect said precondition of said mind by one of the group consisting of meditation, hypnosis, altered mental states or combinations thereof.

11. The article of claim 10, wherein said program is designed to present said scenario in one of the group consisting of: real time, real space, compressed time, compressed space, expanded time, expanded space and combinations thereof.

12. The combination comprising a virtual reality device and a medium with a program imprinted thereon designed for achieving a goal desired by a subject for presenting to at least the visual senses of the subject; said program including:
   at one subliminal stimulus selected from the group of audible subliminal stimulus, visual subliminal stimulus and combinations thereof; and,
   a dynamic scenario, that is designed to communicate in chronological order:
   (I.) a condition which requires a remedy;
   (ii.) a mode for effecting the remedy;
   (iii.) the performance of the mode so as to effect the remedy; and,
   (iv.) rectification of the condition through the performance of the mode; for causing mental visualization with the mind of the subject sufficient for enabling the subject to achieve the desired goal; wherein the goal is selected from the group consisting of: physical learning, mental learning, physical training, mental training, physical healing, mental healing and combinations thereof; operable within the device when the device is mounted on the subject and the medium is operably interfaced with the device, and the program is caused to run. and said program is caused to run.

13. The article of claim 12, wherein the program is further designed to enable interaction between the subject and/or an external operator, and the device.

14. The article of claim 13, wherein said program is further designed to communicate a metaphoric or real, or combined real and metaphoric, scenario to said subject designed for perfecting said mental visualization.

15. The article of claim 12, wherein said program is further designed to effect said precondition said mind by one of the group consisting of meditation, hypnosis, altered mental states or combinations thereof.

16. The article of claim 12, wherein said program is designed to present said scenario in one of the group consisting of: real time, real space, compressed time, compressed space, expanded time, expanded space and combinations thereof.

* * * * *